(12) United States Patent
Tao et al.

(10) Patent No.: US 6,787,281 B2
(45) Date of Patent: Sep. 7, 2004

(54) SELECTED ACID GENERATING AGENTS AND THEIR USE IN PROCESSES FOR IMAGING RADIATION-SENSITIVE ELEMENTS

(75) Inventors: Ting Tao, Fort Collins, CO (US); Jianbing Huang, Trumbull, CT (US)

(73) Assignee: Kodak Polychrome Graphics LLC, Norwalk, CT (US)

( * ) Notice: Subject to any disclaimer, the term of this patent is extended or adjusted under 35 U.S.C. 154(b) by 17 days.

(21) Appl. No.: 10/155,696

(22) Filed: May 24, 2002

(65) Prior Publication Data

US 2003/0219673 A1 Nov. 27, 2003

(51) Int. Cl.[7] ............... G03F 7/021; G03F 7/30; G03C 1/54; C07C 245/20
(52) U.S. Cl. ............ 430/163; 430/157; 430/176; 430/302; 430/270.1; 534/558; 568/28; 522/31; 522/32
(58) Field of Search ............... 430/163, 157, 430/176, 302, 270.1; 534/558; 568/28, 18; 522/31, 32

(56) References Cited

U.S. PATENT DOCUMENTS

| | | | |
|---|---|---|---|
| 4,708,925 A | | 11/1987 | Newman |
| 5,085,972 A | | 2/1992 | Vogel |
| 5,314,747 A | * | 5/1994 | Malhotra et al. ........... 428/341 |
| 5,372,907 A | | 12/1994 | Haley et al. |
| 5,550,004 A | * | 8/1996 | Honda ..................... 430/270.1 |
| 5,814,431 A | | 9/1998 | Nagasaka et al. |
| 5,919,601 A | | 7/1999 | Nguyen et al. |
| 5,932,392 A | | 8/1999 | Hirai et al. |
| 5,945,250 A | | 8/1999 | Aoai et al. |
| 5,965,319 A | | 10/1999 | Kobayashi |
| 6,042,987 A | | 3/2000 | Kobayashi |
| 6,077,641 A | | 6/2000 | Parsons et al. |
| 6,083,658 A | | 7/2000 | Kunita et al. |
| 6,096,124 A | * | 8/2000 | Wong et al. .............. 106/31.43 |
| 6,162,574 A | | 12/2000 | Kobayashi et al. |

FOREIGN PATENT DOCUMENTS

| | | | |
|---|---|---|---|
| JP | 06199770 A | * 7/1994 | ......... C07C/305/22 |
| WO | WO 00/17711 | 3/2000 | |
| WO | WO 02/46507 A2 | 6/2002 | |

OTHER PUBLICATIONS

Aldrich Catalog of Fine Chemical Compounds (1990), p. 1307, 30–359–3.*

* cited by examiner

Primary Examiner—John S. Chu
(74) Attorney, Agent, or Firm—RatnerPrestia

(57) ABSTRACT

An acid generating agent useful for imaging photosensitive elements selected from compounds of formulae (I), (II) and (III).

$$R^5-I^+-R^6 \qquad R^1-X-\overset{O}{\underset{O}{\overset{\|}{Y}}}-O^- \qquad (I)$$

$$R^2-S^+-R^3 \qquad R^1-X-\overset{O}{\underset{O}{\overset{\|}{Y}}}-O^- \qquad (II)$$
$$\underset{R^4}{|}$$

$$Ar^1-N_2^+ \qquad R^1-X-\overset{O}{\underset{O}{\overset{\|}{Y}}}-O^- \qquad (III)$$

wherein $R^1$ is selected from the group consisting of an unsubstituted and substituted hydrocarbon or aryl group;

wherein X is selected from the group consisting of oxygen, sulfur and selenium;

wherein Y is selected from the group consisting of sulfur, selenium and tellurium;

wherein $Ar^1$ is selected from the group consisting of an unsubstituted and substituted aryl group;

wherein $R^2$, $R^3$ and $R^4$ are individually selected from the group consisting of an unsubstituted and substituted hydrocarbon or aryl group or any two of them are bonded together to form a ring structure; and wherein $R^5$ and $R^6$ are individually selected from the group of an unsubstituted and substituted hydrocarbon or aryl group, or are bonded to each other to form a ring structure.

88 Claims, No Drawings

SELECTED ACID GENERATING AGENTS AND THEIR USE IN PROCESSES FOR IMAGING RADIATION-SENSITIVE ELEMENTS

BACKGROUND OF THE INVENTION

1. Field of the Invention

This invention relates to selected acid generating agents useful in radiation-sensitive patterning compositions. The invention relates to such radiation-sensitive patterning compositions as well as methods of imaging radiation-sensitive elements containing such radiation-sensitive patterning compositions.

2. Brief Description of Art

Thermally sensitive, negative working printing plates are generally made with radiation-sensitive patterning compositions that are imaged on a substrate. These patterning compositions commonly contain radiation-sensitive material that is a mixture of an acid generator, a cross-linking resin or compound, a binder resin and an infrared (IR) absorber. Many of the acid generators previously employed in these patterning compositions either contain ozone depletion elements such as fluorine or contain heavy metal such as antimony (Sb) or arsenic (As), which may cause serious environmental contamination problems. Also, some of these previously used acid generators produce volatile acids (e.g., HF, HCl, HBr, HI) that can be easily volatized and lost under conditions of thermal imaging and subsequent optional baking, thereby reducing the cure rate. Such volatile acid loss decreases the efficiency of the printing plates.

Examples of these prior art acid generators are reported in the following:

U.S. Pat. No. 4,708,925 (Newman) describes a photo-solubilizable composition comprising an alkali-soluble phenolic resin and an onium salt. The onium salt imparts a solvent resistance to the phenolic resin that is removed upon exposure to radiation thereby providing a solubility differential between exposed and unexposed areas of the composition. Suitable iodonium salts include iodonium, sulphonium, bromonium, chloronium, oxysulphonium, sulphoxonium, selenonium, telluronium, phosphonium and arsonium salts. Preferably the acid from which the anion is derived has a pKa<5. Suitable inorganic anions include halide anions, bisulfate, tetrafluoroborate, hexafluorophosphate, hexafluoroarsenate and hexafluoroantimonate. Suitable organic anions include those of the formulae: $R^1COO^-$ and $R^1SO_3^-$, in which $R^1$ is an alkyl or aryl. Again, this reference does not teach or suggest the particular acid generators of the present invention.

U.S. Pat. No. 5,372,907 (Haley et al.) describes a radiation-sensitive patterning composition comprising a mixture of (1) a resole, (2) a novolak resin, (3) a latent Bronsted acid (i.e., acid generating agent) and (4) an infrared absorber. In the specification, the latent Bronsted acids in the invention include onium salts, in particular iodonium, sulfonium, phosphonium, selenonium, diazonium and arsonium, with anions such as hexafluorophosphate, hexafluoroantimonate and trifluoromethane sulfonate. However, this reference does not disclose or suggest any latent Bronsted acids of the present invention.

U.S. Pat. No. 5,919,601 (Nguyen et al.) describes a printing plate composition comprising a thermal-activated acid generator; a cross-linking resin; a binder resin comprising a polymer containing reactive pendant groups selected from hydroxyl, carboxylic acid, sulfonamide, and alkoxymethylamide; and an infrared absorber. The composition claims that acid generator is selected from halo alkyl substituted S-triazines and salts containing an onium cation and non-nucleophilic anion, wherein the onium cation is selected from iodonium, sulphonium, phosphonium, oxysulphoxonium, oxysulphonium, sulphoxonium, ammonium and diazonium; the non-nucleophilic anion is selected from tetrafluoroborate, hexafluorophosphate, hexafluoroantimonate, hexafluoroarsenate, triflate, tetrakis(penta-flurophenyl)borate, pentafluoroethyl sulfonate, p-methylbenzenesulfonate, ethyl sulfonate, trifluromethylacetate and pentafluoroethyl acetate. This reference does not disclose or suggest the acid generators of the present invention.

U.S. Pat. No. 5,965,319 (Kobayashi) describes certain onium salt compounds having sulfonic acid as the counter ion to generate sulfonic acid decomposed by light or heat. These onium salts include diazonium sulfonates represented by the following structural formula:

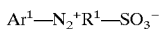

$$Ar^1—N_2^+R^1—SO_3^-$$

wherein $R^1$ represents a hydrocarbon group having 20 or fewer carbon atoms which may be substituted; and $Ar^1$ represents an aryl group having 20 or fewer carbon atoms which may be substituted. This reference does not teach or suggest any of the acid generators of the present invention.

U.S. Pat. No. 6,042,987 (Kobayashi) describes a photosensitive negative image recording material for printing plate having a image recording layer containing a compound which is degraded by the action of light or heat to generate an acid, including an onium salt having a halide, $ClO_4^-$, $PF_6^-$, $BF_4^-$ or sulfonate as a counter ion. There is no knowledge of using the compounds with formulae (I)–(III) in the invention.

WO 00/17711 (IBF Industria Brasileira De Filmes S/A) describes a composition comprising a dual polymer system, an infrared absorbing material, an acid generating compound, and an acid stabilizing compound. The acid generating compounds named therein include, as anions, chloride, bisulfate, hexafluoroantimonate, hexafluorophosphate, tetrafluoroborate, methane sulfonate and mesitylene sulfonate. However, this reference does not teach or suggest acid generating compounds in the present invention.

Huo, H.; Yang, Y.; Yang, L.; Cao, W.; Interaction of diazo resins with sodium dodecyl sulfate in aqueous solutions, *Macromol. Rapid Commun.* 19, 291–294 (1998) details the behavior of diazo resins with sodium dodecyl sulfate (SDS) in aqueous solutions and in films. No mention was made to use such resins to generate acids for catalyzing acid-reactive compositions.

Yang, B.; Cao, W.; Interaction of diphenylamine diazonium salt with sodium dodecyl sulfate in aqueous solution, *J. Colloid and Interface Science* 212, 190–192 (1999) reported photochemical behaviors of diphenylamine diazonium salt with sodium dodecyl sulfate in aqueous solutions. No mention was made to use such resins to generate acids for catalyzing acid-reactive compositions.

Cao, W.; Meng, Z.; Yie, T.; Zhang, D.; Yang, B.; Interaction of sodium dodecyl sulfate with polyelectrolyte complexes derived from diazo resin and sulfonate-containing polymers, *J. Polymer Science: Part A: Polymer Chemistry.* 37, 2601–2606 (1999) reported the results of their studies on the interaction of sodium dodecyl sulfate with polyelectrolyte complexes derived from diazo resin and sulfonate-containing polymers in terms of aqueous solubility and thermal stability of the said complexes. No mention was made to use such resins to generate acids for catalyzing acid-reactive compositions.

Yang, B.; Luo, H.; Cao, W., The thermal decomposition of diazoresin-SDS in aqueous solution or in solid film, *J. Polym. Sco., Part A: Polym. Chem.* 36, 3193–3195 (1998) is concerned with thermal stability of diazoresin-SDS in aqueous solutions or in solid films. No mention was made to use such resins to generate acids for catalyzing acid-reactive compositions.

Accordingly, there is a need for better acid generators that can be used in radiation-sensitive patterning compositions that do not contain environmental questionable elements or produce undesirable volatile acids, yet have a high photolysis efficiency and good photo sensitivity. The present invention provides a solution to that need. In particular, the present invention provides an improved cure rate, processing latitude, processing robustness and long shelf life while maintaining moderate energy requirements of the acid generation step.

BRIEF SUMMARY OF THE INVENTION

Therefore, one aspect of the present invention is directed to an acid generating agent useful for imaging photosensitive elements selected from compounds of formulae (I), (II) and (III):

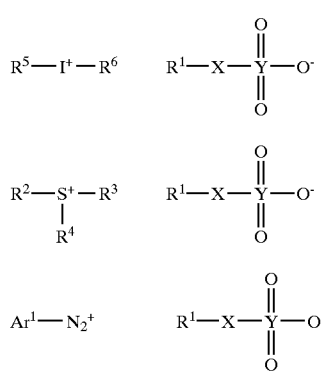

wherein $R^1$ is selected from the group consisting of an unsubstituted and substituted hydrocarbon or aryl group;

wherein X is selected from the group consisting of oxygen, sulfur and selenium;

wherein Y is selected from the group consisting of sulfur, selenium and tellurium;

wherein $Ar^1$ is selected from the group consisting of an unsubstituted and substituted aryl group;

wherein $R^2$, $R^3$ and $R^4$ are individually selected from the group consisting of an unsubstituted and substituted hydrocarbon or aryl group or any two of them are bonded together to form a ring structure; and wherein $R^5$ and $R^6$ are individually selected from the group of an unsubstituted and substituted hydrocarbon or aryl group, or are bonded to each other to form a ring structure.

Another aspect of the present invention is directed to a radiation-sensitive patterning composition comprising:

(1) at least one acid generating compound selected from the compounds of formulae (I), (II) and (III):

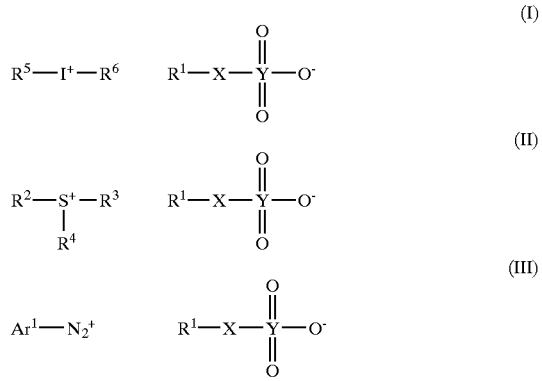

(2) at least one cross-linking agent cross-linkable by an acid;

(3) at least one polymer compound having at least one functional group capable of reacting with the cross-linking agent; and (4) at least one infrared absorbing compound;

wherein $R^1$ is selected from the group consisting of an unsubstituted and substituted hydrocarbon or aryl group;

wherein X is selected from the group consisting of oxygen, sulfur and selenium;

wherein Y is selected from the group consisting of sulfur, selenium and tellurium;

wherein $Ar^1$ is selected from the group consisting of an unsubstituted and substituted aryl group;

wherein $R^2$, $R^3$ and $R^4$ are individually selected from the group consisting of an unsubstituted and substituted hydrocarbon or aryl group or any two of them are bonded together to form a ring structure; and wherein $R^5$ and $R^6$ are individually selected from the group of an unsubstituted and substituted hydrocarbon or aryl group, or are bonded to each other to form a ring structure.

Still another aspect of the present invention is directed to a radiation-sensitive imaging element comprising a lithographic substrate having a layer of the above-noted radiation-sensitive patterning composition coated thereon.

Yet another aspect of the present invention is directed to a process of imaging a photosensitive element comprising the steps of:

(1) providing a radiation-sensitive imaging element comprising a lithographic substrate having a layer of above-noted radiation-sensitive patterning composition thereon;

(2) imagewise exposing the radiation-sensitive imaging element; and (3) removing unexposed areas of the radiation-sensitive patterning composition layer from the lithographic substrate, leaving a negative-working imaging element.

Optionally, the imaged radiation-sensitive imaging element may be baked after step (2) and before step (3) at a temperature and time period sufficient to produce a cured element.

One of the advantages of the present invention is that the present acid generators do not contain either ozone depletion elements such as fluorine or heavy metals such as antimony (Sb) or arsenic (As), which may cause environmental contamination problems if improperly used. Another advantage of the present invention is that the present generated acids are non-volatile at elevated operating temperatures, thus the loss of acid by evaporation is minimized. Still further, the photosensitive compositions of the present invention provide excellent photographic sensitivity and photolysis efficiency. In particular, the present invention allows for improved curing rate, processing latitude and robustness of thermal preheated negative working patterning compositions especially printing plates, while maintaining adequate shelf life.

The present radiation-sensitive composition can be used in various types of lithography including photomask lithography, imprint lithography, microelectronic and microoptical devices, printed circuit boards and especially radiation-sensitive lithographic plates.

DETAILED DESCRIPTION OF THE INVENTION

I. Radiation-Sensitive Patterning Compositions

As stated above, the radiation-sensitive patterning compositions comprise a mixture of at least four components plus optionally other compounds. These ingredients are preferably as follows:

(A) Acid Generating Compounds

In the above-mentioned general formulae (I), (II) and (III), $R^1$ preferably represents a hydrocarbon or aryl group having 50 or fewer carbon atoms, which may be substituted.

Examples of alkyl groups and aryl groups represented by $R^1$ include alkyl groups such as methyl group, ethyl group, n-propyl group, isopropyl group, allyl group, n-butyl group, sec-butyl group, t-butyl group, hexyl group, cyclohexyl group, heptyl group, octyl group, 2-ethylhexyl group, nonyl group, decyl group, dodecyl group, hexadecyl group and octadecyl group; alkenyl groups such as vinyl group, 1-methylvinyl group, and 2-phenylvinyl group; aralkyl groups such as benzyl group, vinyl benzyl group and phenethyl group; and aryl groups such as phenyl group, tolyl group, xylyl group, cumenyl group, mesityl group, dodecylphenyl group, phenylphenyl group, naphthyl group, and anthracenyl group.

These alkyl or aryl groups may have a substituent such as a halogen atom, hydroxy group, alkoxy group, aryloxy group, nitro group, cyano group, carbonyl group, carboxyl group, alkoxycarbonyl group, anilino group, and acetamido group. Examples of groups having a substituent include trifluoromethyl group, 2-methoxyethyl group, 10-camphornyl group, fluorophenyl group, chlorophenyl group, bromophenyl group, iodophenyl group, methoxyphenyl group, hydroxyphenyl group, phenoxyphenyl group, nitrophenyl group, cyanophenyl group, carboxyphenyl group, methoxynaphthyl group, dimethoxyanthracenyl group, diethoxyanthracenyl group, and anthraquinonyl group.

$Ar^1, R^2, R^3, R^4, R^5$ and $R^6$ may each preferably represent an aryl group having 50 or fewer carbon atoms, which may be substituted.

Examples of aryl groups represented by $Ar^1, R^5$ or $R^6$ include a phenyl group, tolyl group, xylyl group, cumenyl group, mesityl group, dodecylphenyl group, phenylphenyl group, naphthyl group, anthracenyl group, fluorophenyl group, chlorophenyl group, bromophenyl group, iodophenyl group, methoxyphenyl group, hydroxyphenyl group, phenoxyphenyl group, nitrophenyl group, cyanophenyl group, carboxyphenyl group, anilinophenyl group, anilinocarbonylphenyl group, morpholinophenyl group, phenylazophenyl group, methoxynaphthyl group, hydroxynaphthyl group, nitronaphthyl group, and anthraquinonyl group.

$R^2, R^3, R^4, R^5$ and $R^6$ may each represent a hydrocarbon group having 50 or fewer carbon atoms which may be substituted.

Examples of unsubstituted and substituted alkyl and aryl groups represented by $R^2, R^3, R^4, R^5$ and $R^6$ include methyl group, ethyl group, n-propyl group, isopropyl group, allyl group, n-butyl group, sec-butyl group, t-butyl group, hexyl group, cyclohexyl group, benzyl group, phenyl group, tolyl group, t-butylphenyl group, naphthyl group, anthracenyl groups; 2-methoxyethyl group, fluorophenyl group, chlorophenyl group, bromophenyl group, iodophenyl group, methoxyphenyl group, hydroxyphenyl group, phenylthiophenyl group, hydroxynaphthyl group, methoxynaphthyl group, benzoylmethyl group, and naphthoylmethyl group.

$R^2$ and $R^3$ or $R^2$ and $R^4$ or $R^3$ and $R^4$ or $R^5$ and $R^6$ may be bonded each other to form a ring.

Preferred examples of a cationic portion of the onium salts represented by the general formula (I) to (III) include an iodonium ion, sulfonium ion, and diazonium ion. Preferred examples of the structure of the cationic portions of these onium salts are illustrated in U.S. Pat. Nos. 5,965,319 (see columns 3 to 10) and 6,162,574.

The counter anions of the present invention are preferably organic sulfates (when X=oxygen and Y=sulfur) or organic thiosulfates (when X=Y=sulfur). Examples of organic sulfate anions include:

(1) methyl sulfate
(2) ethyl sulfate
(3) 1-propyl sulfate
(4) 2-propyl sulfate
(5) N-butyl sulfate
(6) allyl sulfate
(7) 10-camphor sulfate
(8) trifluoromethyl sulfate
(9) pentafluoroethyl sulfate
(10) benzyl sulfate
(11) P-tolyl sulfate
(12) 3-methoxybenzyl sulfate
(13) 4-methoxybenzyl sulfate
(14) 4-hydroxybenzyl sulfate
(15) 4-chlorobenzyl sulfate
(16) 3-nitrobenzyl sulfate
(17) 4-nitrobenzyl sulfate
(18) 4-acetylbenzyl sulfate
(19) pentafluorobenzyl sulfate
(20) 4-dodecylbenzyl sulfate
(21) mesitylene sulfate
(22) 2,4,6-triisopropyl benzyl sulfate
(23) 2-hydroxy-4-methoxybenzophenone-5-sulfate
(24) dimethyl isophthalate-5-sulfate
(25) diphenyl amine-4-sulfate
(26) 1-naphthalene sulfate
(27) 2-naphthalene sulfate
(28) 2-naphthol-6-sulfate
(29) 2-naphthol-7-sulfate
(30) anthraquinone-1-sulfate
(31) anthraquinone-2-sulfate
(32) 9,10-dimethoxyanthracene-2-sulfate
(33) 9,10-diethoxyanthracene-2-sulfate
(34) quinoline-8-sulfate

(35) 8-hydroxyquinoline-5-sulfate
(36) 8-anilino-naphthalene-1-sulfate
(37) dodecyl sulfate
(38) hexadecyl sulfate
(39) vinyl benzyl sulfate Examples of organic thiosulfate anions include the same compounds 1–39 where a thiosulfate is substituted for sulfate moiety.

Onium alkyl or aryl sulfates preferably used in the present invention can be obtained by salt exchange by mixing a corresponding onium $Cl^-$, $Br^-$, $F^-$, $I^-$, or $HSO_4^-$ salt with sodium alkyl or aryl sulfate or potassium alkyl or aryl sulfate in water or a solvent including water and a hydrophilic solvent such as alcohol.

Onium alkyl or aryl thiosulfates preferably used in the present invention can be obtained by mixing a corresponding onium $Cl^-$, $Br^-$, $F^-$, $I^-$, or $HSO_4^-$ salt with sodium alkyl or aryl thiosulfate or potassium alkyl or aryl thiosulfate in water or a solvent including water and a hydrophilic solvent such as alcohol.

These acid generating compounds are present in radiation-sensitive patterning compositions of the present invention in an amount of 0.01 to 50% by weight, preferably 0.1 to 25% by weight, and more preferably 0.5 to 20% by weight based on the total solid components of the patterning composition. In a case in which the amount added is less than 0.01% by weight, an image cannot be obtained, and, in a case in which the amount added is more than 50% by weight, a stain is produced in a nonimage formation portion at the time of printing, and thus neither is preferable.

(B) Cross-Linking Agents Cross-Linkable by an Acid

Cross-linking agents cross-linkable by an acid preferably used in the present invention (hereinafter referred to as a cross-linking agent) are compounds having, in a molecule, at least two groups bonded to a benzene ring, such as a hydroxymethyl group, alkoxymethyl group, epoxy group, and vinyl ether group. Examples thereof include methylol melamine, resol resin, epoxidized novolak resin, and urea resin. Other examples include amino resins having at least 2 alkoxymethyl groups (e.g. alkoxymethylated melamine resin, alkoxymethylated glycoluril and alkoxymethylated benzoguanamine). Furthermore, compounds disclosed in "Kakyozai Handbook (Cross-linking Agent Handbook)", by Shinzo Yamashita and Tosuke Kaneko, published by Taiseisha, Co., Ltd., are also preferable. In particular, phenol derivatives having, in a molecule, at least two groups bonded to a benzene ring such as a hydroxymethyl group and alkoxymethyl group provide good fastness in an image portion when an image is formed, and thus are preferable. Examples of phenol derivatives include resol resin. Preferred resole resins would be GP649D99 resole resin available from Georgia Pacific and BKS-5928 resole resin available from Union Carbide Corporation.

However, these cross-linking agents are unstable with respect to heat, and thus they are not very favorable in terms of storability after the production of an image recording material. On the other hand, phenol derivatives having, in a molecule, at least two groups bonded to a benzene ring such as a hydroxymethyl group and alkoxymethyl group, and 3 to 5 benzene rings with a molecular weight of 1,200 or less have good storability, and thus are most preferably used in the present invention.

As an alkoxymethyl group, those having 6 or fewer carbon atoms are preferable. Examples thereof include a methoxymethyl group, ethoxymethyl group, n-propoxymethyl group, isopropoxymethyl group, n-butoxymethyl group, isobutoxymethyl group, sec-butoxymethyl group, and t-butoxymethyl group. Furthermore, alkoxy groups having an alkoxy substituent or alkoxy substituents such as a 2-methoxyethoxy group, and 2-methoxy-1-propyl group are also preferable.

Among these phenol derivatives, particularly preferable ones are illustrated in U.S. Pat. No. 5,965,319 (columns 31–38).

Phenol derivatives having a hydroxymethyl group can be obtained by the reaction of a corresponding phenol compound without a hydroxymethyl group and formaldehyde in the presence of a base catalyst. At the time, it is preferable that a reaction temperature be 60° C. or less so as to prevent resinification or gelation of the phenol derivative. Specifically, the phenol derivatives having a hydroxymethyl group can be synthesized by methods disclosed in Japanese Patent Application Laid-Open (JP-A) Nos. 6-282067 and 7-64285.

Phenol derivatives having an alkoxymethyl group can be obtained by the reaction of a corresponding phenol derivative having a hydroxymethyl group and alcohol in the presence of an acid catalyst. At the time, it is preferable that a reaction temperature be 100° C. or less so as to prevent resinification or gelation of the phenol derivative. Specifically, the phenol derivatives having an alkoxymethyl can be synthesized by a method disclosed in European Patent (EP) No. 632,003A1.

The phenol derivatives having a hydroxymethyl group or an alkoxymethyl group synthesized as mentioned above are preferable in terms of storability. The phenol derivatives having an alkoxymethyl group are particularly preferably in terms of storability.

One particularly preferred cross-linking agent is terephthaldicarboxaldehyde.

In the present invention, a cross-linking agent is used in the amount of 5 to 70% by weight, and preferably 10 to 65% by weight based on the total solids of the radiation-sensitive material. In a case in which the amount of the cross-linking agent is less than 5% by weight, the film strength of the image portion at the time of image recording deteriorates. On the other hand, an amount more than 70% by weight is not preferable in terms of storability.

These cross-linking agents can be used alone or in a combination of two or more.

(C) Polymer Compounds Capable of Reacting with said Cross-Linking Agent

Any polymer capable of reacting with the cross-linking agent to prepare suitable radiation-sensitive patterning compositions may be employed in the present invention. One preferred class of these polymers is polymer compounds having an alkaline-soluble group in the molecule. These polymer compounds having an alkaline-soluble group as used in the present invention (hereinafter referred to as alkaline-soluble polymer compound) mean resins having an alkaline-soluble group in a molecule, such as a novolak resin, acetone-pyrogallol resin, polyhydroxystyrenes, hydroxystyrene-N-substituted maleimide copolymer, hydroxystyrene-maleic anhydride copolymer, and polymer compound such as an acrylic copolymer or a urethane type polymer having an alkaline-soluble group, whose monomers include 1 mol % or more of a component unit having an acidic group such as an acrylic acid. Examples of an alkaline-soluble group here include a carboxyl group, phenolic hydroxyl group, sulfonic acid group, phosphonic acid group, imide group, carbamate groups and sulfonamide groups.

Novolak resins are resins obtained by the condensation of phenols and aldehydes under an acidic condition. Examples of preferable novolak resins include novolak resin obtained from phenol and formaldehyde, novolak resin obtained from m-cresol and formaldehyde, novolak resin obtained from o-cresol and formaldehyde, novolak resin obtained from octylphenol and formaldehyde, novolak resin obtained from m-/p- mixed cresol and formaldehyde, novolak resin obtained from a mixture of phenol/cresol (either of m-, p-, o-, or m-/p-, m-/o-, o-/p- mixed) and formaldehyde, novolak resin obtained from resorcinol and formaldehyde, and novolak resin obtained from phenol/resorcinol and formaldehyde. It is preferable that these novolak resins have a weight-average molecular weight of 800 to 200,000 and a number-average molecular weight of 400 to 60,000.

In a case in which a polymer, at least one of whose monomers is hydroxystyrene such as poly-p-hydroxystyrene, poly-m-hydroxystyrene, p-hydroxystyrene-N-substituted maleimide copolymer, and p-hydroxystyrene-maleic anhydride copolymer is used, it is preferable that the weight-average molecular weight be 2,000 to 500,000, and preferably 4,000 to 300,000.

Examples of acrylic copolymers having an alkaline-soluble group include methacrylic acid-allylmethacrylate copolymer, methacrylic acid-benzylmethacrylate copolymer, methacrylic acid-hydroxyethylmethacrylate copolymer, poly(hydroxyphenyl methacrylamide), poly(hydroxyphenylcarbonyloxyethyl acrylate), and poly(2,4-dihydroxyphenyl carbonyloxyethyl acrylate). These acrylic resins are resins whose monomers include a component unit having, in a molecule, an acidic group such as carboxyl group and hydroxyphenyl group. Resins whose component units include 1 mol % or more of (meth)acrylic acid, hydroxystyrene, and hydroxyphenyl (meth)acrylamide based on the total component units and whose weight-average molecular weight is 2,000 to 500,000, preferably 4,000 to 300,000 is preferable.

Examples of urethane type polymers having an alkaline-soluble group include a resin obtained by the reaction of diphenylmethane diisocyanate, hexamethylene diisocyanate, tetraethylene glycol, and 2,2-bis(hydroxymethyl) propionic acid. It is preferable that the urethane-type polymer be a resin whose monomer include a component unit having an acidic group such as carboxylic acid and a hydroxyphenyl group in a molecule in an amount of 1 mol % or more.

Among these examples of alkaline soluble polymer compounds, novolak resins are preferable in terms of the durability of the form plate. On the other hand, polymers whose monomers include hydroxystyrene and acrylic copolymers having an alkaline-soluble group are preferable in terms of developing properties.

In the present invention, the amount of these alkaline soluble polymer compounds is 10 to 90% by weight, preferably 20 to 85% by weight, and more preferably 30 to 80% by weight based on the total solids of the radiation-sensitive patterning composition. If the amount of the alkaline soluble polymer compound is less than 10% by weight, the durability of the radiation-sensitive layer deteriorates. On the other hand, an amount more than 90% by weight is not preferable in terms of either sensitivity or durability.

These alkaline soluble polymer compounds can be used alone or in a combination of two or more.

While not wishing to be bound by theory, it is believed that the cross-linking and binder resins are co-reactive resins. The designations of "crosslinking resins" and "binder resin" may therefore be used interchangeably and, in some cases, one resin may act as both a "crosslinking resin" and as a "binder resin."

(D) Infrared Absorbing Compounds

Infrared ray absorbing compounds used in the present invention are a dye or pigment effectively absorbing an infrared ray having a wavelength of 760 nm to 1,200 nm. It is preferable that the dye or pigment have an absorption maximum between the wavelengths of 760 nm and 1,200 nm.

As dyes, known dyes commercially available or those disclosed in the literature (such as "Senryo Binran (Dye Handbook)" edited by Yuki Gosei Kagaku Kyokai (Organic Synthetic Chemistry Association), published in 1970, can be used. Specifically, examples include azo dyes, metal complex azo dyes, pyrazolone azo dyes, anthraquinone dyes, phthalocyanine dyes, carbonium dyes, quinoneimine dyes, methyne dyes, cyanine dyes, and metal thiolate complexes.

Examples of preferable dyes include cyanine dyes disclosed in Japanese Patent Application Laid-Open (JP-A) Nos. 58-125246, 59-84356, 59-202829, and 60-78787; methyne dyes disclosed in Japanese Patent Application Laid-Open (JP-A) Nos. 58-173696, 58-181690, and 58-194595; naphthoquinone dyes disclosed in Japanese Patent Application Laid-Open (JP-A) Nos. 58-112793, 58-224793, 59-48187, 59-73996, 60-52940, and 60-63744; squalilium dyes disclosed in Japanese Patent Application Laid-Open (JP-A) No. 58-112792; and cyanine dyes disclosed in U.K. Patent No. 434,875.

Furthermore, near infrared absorption sensitizing agents disclosed in U.S. Pat. No. 5,156,938 can be preferably used. Moreover, substituted aryl benzo(thio)pyrylium salts disclosed in U.S. Pat. No. 3,881,924; trimethyne thiapyrylium salts disclosed in Japanese Patent Application Laid-Open (JP-A) No. 57-142645 (U.S. Pat. No. 4,327,169); pyrylium-containing compounds disclosed in Japanese Patent Application Laid-Open (JP-A) Nos. 58-181051, 58-220143, 59-41363, 59-84248, 59-84249, 59-146063, and 146061; cyanine dyes disclosed in Japanese Patent Application Laid-Open (JP-A) No. 59-216146; pentamethyne thiopyrylium salts disclosed in U.S. Pat. No. 4,283,475; and pyrylium compounds disclosed in Japanese Patent Application Publication Nos. 5-13514 and 5-19702 can be preferably used as well.

As other examples of preferable dyes, near infrared absorption dyes disclosed U.S. Pat. No. 4,756,993 represented by formulas (I) and (II) can be presented.

Among these dyes, particularly preferable are cyanine dyes, squarylium dyes, pyrylium salts, and nickel thiolate complexes.

Preferably, these IR dyes contain anions that do not form volatile acids in the presence of other strong acids.

Pigments usable in the present invention include commercially available pigments and those disclosed in the Color Index (C. I.) Manual, "Saishin Ganryo Binran (Modern Pigment Manual)" edited by Nippon Ganryo Gijutsu Kyokai (Japan Pigment Technology Association), published in 1977; "Ganryo Oyo Gijutsu (Modern Pigment Application Technology)" by CMC Press, published in 1986; and "Insatsu Ink Gijutsu (Printing Ink Technology)" by CMC Press, published in 1984.

Examples of pigments include black pigments, yellow pigments, orange pigments, brown pigments, red pigments, purple pigments, blue pigments, green pigments, fluorescent pigments, metal powder pigments, and polymer bond pigments. Specifically, insoluble azo pigments, azo lake pigments, condensation azo pigments, chelate azo pigment, phthalocyanine pigments, anthraquinone pigments, perylene and perynone pigments, thioindigo pigments, Paris Blue pigment, Prussian Blue pigment, quinacridone pigments, dioxazine pigments, isoindolinone pigments, quinophthalone pigments, colored lake pigments, azine pigments, nitroso pigments, nitro pigments, natural pigments, fluorescent pigments, inorganic pigments, and carbon black can be used. Among these examples, carbon black is preferable.

These pigments can be used without surface treatment, or can be used after being applied with surface treatment. Examples of surface treatment methods include a method of surface coating with a resin or a wax, a method of adhering a surfactant, and a method of bonding a reactive substance (such as a silane coupling agent, an epoxy compound, and polyisocyanate) with the pigment surface. The above-mentioned surface treatment methods are disclosed in "Kinzokusekken no Seishitsu to Oyo (Natures and Applications of Metal Soaps)" by Sachi Press; "Insatsu Ink Gijutsu (Printing Ink Technology)" by CMC Press; published in 1984; and "Saishin Ganryo Oyo Gijutsu (Modern Pigment Application Technology)" by CMC Press, published in 1986.

A pigment particle size of 0.01 $\mu$m to 10 $\mu$m is preferable, 0.05 $\mu$m to 1 $\mu$m is more preferable, and 0.1 $\mu$m to 1 $\mu$m is the most preferable. A pigment particle size smaller than 0.01 $\mu$m is not preferable in terms of the stability of the pigment dispersion in a photosensitive layer coating solution. On the other hand, a pigment particle size larger than 10 $\mu$m is not preferable in terms of the uniformity of the image recording layer.

As methods of dispersing a pigment, known dispersing methods employed in ink production or toner production can be used. Examples of dispersing machines include ultrasonic dispersing machines, sand mills, attritors, pearl mills, super mills, ball mills, impellers, dispersers, KD mills, colloid mills, dynatrons, triple roll mills, and pressure kneaders. Details thereof are described in "Saishin Ganryo Oyo Gijutsu (Modern Pigment Application Technology)" by CMC Press, published in 1986.

These dyes or pigments can be added in an amount of 0.01 to 50% by weight based on the total solids of the radiation-sensitive patterning material, preferably in an amount of 0.1 to 10% by weight, more preferably in an amount of 0.5 to 10% by weight in the case of a dye, and more preferably in an amount of 0.1 to 10% by weight in the case of a pigment. An amount of a pigment or dye less than 0.01% by weight causes low sensitivity. On the other hand, an amount more than 50% by weight produces stains in a nonimage portion at the time of printing.

These dyes or pigments can be added in a layer with other components or, in a case in which the image recording material comprises a plurality of layers, can be added in a layer which is different from a layer containing the other components.

While IR absorbers are generally required for most preferred applications, new developments with dynamic mirrors and UV lasers may allow for radiation-sensitive compositions of the present invention that do not require IR absorbers, but only need the above-noted first three components. Accordingly, one embodiment of the present invention encompasses this alternative composition and its use with these new imaging techniques.

(E) Other Components

In the present invention, the above-mentioned four components (A) to (D) are necessary, and various compounds can be added to the radiation-sensitive patterning material as needed.

For example, a dye having a large absorption in the visible light region can be used as the coloring agent.

Specifically, examples include Oil Yellow #101, Oil Yellow #103, Oil Pink #312, Oil Green BG, Oil Blue BOS, Oil Blue #603, Oil Black BY, Oil Black BS, Oil Black T-505 (manufactured by Orient Chemical Industry, Co., Ltd.), Victoria Pure Blue, Crystal Violet (CI42555), Methyl Violet (CI42535), Ethyl Violet, Rhodamine B (CI145170B), Malachite Green (CI42000), Methylene Blue (CI52015), and dyes disclosed in Japanese Patent Application Laid-Open (JP-A) No. 62-293247.

It is preferable to add these dyes for easily distinguishing the image portion and the nonimage portion after image formation. Preferably, these visible dyes and colorant agents contain anions that do not form volatile acids in the presence of other strong acids. The amount to be added is 0.01 to 10% by weight based on the total solid component of the image recording material.

In order to enable stable treatment regardless of the fluctuation in development conditions, a nonionic surfactant disclosed in Japanese Patent Application Laid-Open (JP-A) Nos. 62-251740 and 3-208514 and an ampholytic surfactant disclosed in Japanese Patent Application Laid-Open (JP-A) Nos. 59-121044 and 4-13149 can be added to an image recording material of the present invention.

Examples of nonionic surfactants include sorbitan tristearate, sorbitan monopalmitate, sorbitan trio late, mono glyceride stearate, and polyoxyethylene nonylphenyl ether.

Examples of ampholytic surfactants include alkyl di(aminoethyl)glycine, alkyl polyaminoethylglycine hydrochloride, 2-alkyl-n-carboxyethyl-N-hydroxyethyl imidazolinium betaine, and N-tetradecyl-N,N-substituted betaine (for example, Amorgen K manufactured by Dai-Ichi Kogyo Co., Ltd.).

The amount of the above-mentioned nonionic surfactants and ampholytic surfactants is preferably 0.05 to 15% by weight, and more preferably 0.1 to 5% by weight in a radiation-sensitive patterning material.

In order to provide flexibility to the film, and the like, a plasticizer can be added as needed to the image recording material of the present invention. Examples of a plasticizer include butylphthalyl, polyethylene glycol, tributyl citrate, diethyl phthalate, dibutyl phthalate, dihexyl phthalate, dioctyl phthalate, tricresyl phosphate, tributyl phosphate, trioctyl phosphate, tetrahydrofurfuryl oleate, an oligomer and a polymer of acrylic acid or methacrylic acid.

In addition to these examples, the above-mentioned onium salts, haloalkylated s-triazines, epoxy compounds, vinyl ethers, phenol compounds having an alkoxy methyl group and phenol compounds having a hydroxymethyl group disclosed in Japanese Patent Application No. 7-18120, can also be added.

An image recording material of the present invention can be produced, in general, by dissolving the above-mentioned component in a solvent and applying the resultant solution to an appropriate support. Solvents used herein include, but are not limited to, ethylene dichloride, cyclohexanone, methyl ethyl ketone, methanol, ethanol, propanol, ethylene glycol monomethyl ether, 1-methoxy-2-propanol, 2-methoxy ethyl acetate, 1-methoxy-2-propyl acetate, dimethoxyethane, methyl lactate, ethyl lactate, N,N-dimethyl acetamide, N,N-dimethyl formamide, tetramethyl urea, N-methyl pyrolidone, dimethyl sulfoxide, sulfolane, gamma.-butyl lactone, toluene, acetone and water.

These solvents are used alone or as a mixture. The concentration of the above-mentioned components (total solid components including additives) is preferably 1 to 50% by weight in the solution. The application amount (solid component) on the support obtained after applying and drying is determined according to the application purpose. However, as to the planographic printing plate, in general, 0.5 to 5.0 g/m² is preferable and 1 to 2.5 g/m² is more preferable. As a method of application, various methods can be used, such as bar coater application, rotation application, spray application, curtain application, dip application, air knife application, blade application, and roll application. As the application amount decreases, the apparent sensitivity increases, but the film characteristic of the image recording film decreases.

A surfactant for improving the applicability, such as a fluorine-containing surfactant disclosed in Japanese Patent Application Laid-Open (JP-A) No. 62-170950 can be added to an image recording layer of the present invention. An addition amount is preferably 0.01 to 1% by weight based on the total solid component of the radiation-sensitive patterning composition, and more preferably 0.05 to 0.5% by weight.

II. Lithographic Substrates

Examples of a support used in the present invention include dimensionally stable plate-like substances such as paper, paper laminated with plastic (such as polyethylene, polypropylene, and polystyrene), metal plates (such as aluminum, zinc, and copper), plastic films (such as cellulose diacetate, cellulose triacetate, cellulose propionate, cellulose butyrate, cellulose acetate/butyrate, cellulose nitrate, polyethylene terephthalate, polyethylene, polystyrene, polypropylene, polycarbonate, and polyvinyl acetal), and paper or plastic film laminated or deposited with the above-mentioned metals.

A polyester film or an aluminum plate is preferable as a support in the present invention. In particular, an aluminum plate is preferable since it has good dimensional stability and can be provided at a relatively low cost. Examples of preferable aluminum plates include pure aluminum plates and alloy plates comprising aluminum as the main component and trace quantities of a different element. Furthermore, plastic films to which aluminum is laminated or deposited can also be used. Examples of different elements included in an aluminum alloy include silicon, iron, manganese, copper, magnesium, chrome, zinc, bismuth, nickel, and titanium. An amount of the different element in the alloy is preferably 10% by weight or less. In the present invention, pure aluminum is particularly preferable. However, since production of a completely pure aluminum is difficult in terms of refining technology, one containing trace quantities of a different element can be used. The composition of an aluminum plate applied in the present invention as mentioned above is not specifically defined, and a known aluminum plate can be also used. The thickness of an aluminum plate used in the present invention is about 0.1 mm to 0.6 mm, preferably 0.15 mm to 0.4 mm, and more preferably 0.2 mm to 0.3 mm.

When an aluminum plate is used as the support, it is desirable to conduct a roughening treatment prior to the coating with a polymer first layer. Also, prior to roughening of the aluminum plate, a degreasing treatment with a surfactant, an organic solvent, or an aqueous alkaline solution is conducted for removing the rolling oil on the surface as needed.

The surface roughening treatment of an aluminum plate can be implemented using various methods, such as a mechanically roughening method, an electrochemically roughening method in which a plate surface is dissolved, and a chemically roughening method in which a plate surface is dissolved selectively. As a mechanical method, known methods such as a ball abrasion method, brush abrasion method, blast abrasion method, and buff abrasion method can be used. As an electrochemically roughening method, a method in which an alternating current or direct current is applied to a plate in an electrolytic solution containing a hydrochloric acid or nitric acid can be used. Further, a method combining both of the above-mentioned methods as disclosed in Japanese Patent Application Laid-Open (JP-A) No. 54-63902 can be used.

An aluminum plate to which surface roughening treatment is applied may be subjected to an alkaline etching treatment or a neutralizing treatment, if necessary, followed by an anodizing treatment so as to improve the water retention property and the abrasion resistance property of the surface, if desired. As an electrolyte used in the anodizing treatment of an aluminum plate, various electrolytes which form a porous oxide film can be used. In general, sulfuric acid, phosphoric acid, oxalic acid, chromic acid, or a mixture thereof can be used. The concentration of an electrolyte is suitably decided according to the type of electrolyte.

The treatment conditions of the anodization may not be specified since they significantly change depending on the type of electrotype solution used. In general, conditions of an electrolyte solution concentration of 1 to 80% by weight, a solution temperature of 5 to 70° C., a current density of 5 to 60 A/dm², a voltage of 1 to 100 V, and an electrolysis duration of 10 seconds to 5 minutes are appropriate.

If the amount of film produced by anodization, durability of the plate may be insufficient, less than 1.0 g/m², and scratches may be easily produced in a non-image portion of the planographic printing plate and, thereby, so-called "scratch toning" in which ink adheres to such scratches in printing.

After the anodizing treatment, hydrophilic treatment is applied to the aluminum surface, if necessary. Examples of a hydrophilic treatment used in the present invention include an alkaline metal silicate (such as an aqueous solution of sodium silicate) method as disclosed in U.S. Pat. Nos. 2,714,066, 3,181,461, 3,280,734, and 3,902,734. In this method, the support (aluminum plate) is treated by immersing or electrolysis with an aqueous solution of sodium silicate. Other examples include a method of treating with potassium fluorozirconate disclosed in Japanese Patent Application Publication (JP-B) No. 36-22063 and a method of treating with polyvinyl phosphonate disclosed in U.S. Pat. Nos. 3,276,868, No. 4,153,461, and 4,689,272.

III. Processes of Imaging

The patterning composition is coated onto the above-noted substrate by any known coating technique. Examples of such coating technology include rotation or spin coating, slot coating wire bar coating, dip coating, air knife coating, roll coating, blade coating, curtain coating and the like. The preferred method is slot coating.

The patterning composition is preferably dried to a suitable temperature to remove excess solvent. This drying may be carried out in a hot air drier or infrared ray dryer and the like, preferably at temperatures from about 40° C. to about 150° C. for 30 seconds to 10 minutes.

The thickness of the resulting layer, after drying, on the support can vary widely, but it is typically in the range from about 0.5 to about 3 microns, more preferably, from about 1 to about 2 microns.

No other essential layers are provided on the substrate. In particular, there need be no protective or other type of layers over the patterning composition layer. Optional, but not preferred, antihalation layers may be disposed under the imaging layer, or on the backside of the support (such as when the support is a transparent polymeric film).

The second step of the present process subjected the patterning composition layer to sufficient actinic radiation (e.g. 180 nm to 1200 nm) to imagewise expose that layer. The actinic radiation may be any radiation that will image this layer, including infrared (IR), ultra-violet and visible light. The sensitive material is preferably exposed to infrared radiation (IR) by scanning a laser beam modulated by an image signal. This IR imaging may be carried out by well-known methods. For example, the patterning composition layer may be imaged with a laser or an array of lasers emitting modulated near IR or IR radiation in a wavelength region that is absorbed by the absorber. IR radiation, especially IR radiation in the range of 750 to 1200 nm, preferably about 800 nm to about 1125 nm, is typically used for imaging thermally imageable elements. Imaging is conveniently carried out with a laser emitting at about 830 or at about 1056 nm. The IR exposure energy is preferably from about 30 to about 500 mJ/cm$^2$; more preferably from about 30 to about 350 mJ/cm$^2$, and most preferably from about 50 to about 175 mJ/cm$^2$. Suitable commercially available imaging devices include imagesetters such as the Creo Trendsetter (CREO, British Columbia, Canada), the Gerber Crescent 42T (GERBER, Brussels, Belgium) and Platerite 8000 (SCREEN, Rolling Meadows, Ill.). While IR exposure is the preferred actinic radiation source, conventional UV light or visible light sources may also be used. These include carbon arc lamps, mercury vapor lamps, fluorescent lamps, tungsten lamps and photoflood lamps operating in the UV/visible light spectrum between 250 and 700 nm.

Alternatively, the patterning composition layer may be imaged using an apparatus containing a heated stylus or a thermal printing heat. A suitable commercially hot stylus imaging device is the GS 618-400 thermal plotter (OYO Instruments, Houston, Tex.). When exposure is carried out with a thermal head, it is unnecessary that the element contains the IR absorber. However, elements that do can still be imaged with the thermal head.

After the imagewise radiation or exposure, the patterning composition may be optionally heated. This optional heating operation can be effected by radiation, convection, contact with heated surfaces, for example, with rollers, or by immersion in a heated bath comprising an inert liquid, for example, water. The temperature range will be set around the fog point of the plate containing the patterning composition. The fog point is defined as the minimum amount of heat energy required to render a thermal plate non-processable. Preferably, the applied heat energy is ±50° F. from the fog point, more preferably ±30° F. from the fog point and most preferably ±15° F. from the fog point. The duration of heating can vary widely, depending on the method chosen for the application of heat as well as the other steps in the process. If a heat-transferring medium is used, the heating time will preferably be from about 30 seconds to about 30 minutes, more preferably from about 1 minute to about 5 minutes.

The next step of the present process is developing the exposed patterned composition layer with an aqueous developing solution. The developing solution used for the development processing may be any liquid or solution that can penetrate and remove the unexposed regions without substantially affecting the complimentary exposed regions. While not being bound by any theory or explanation, it is believed that image discrimination is based on kinetic effect. The unexposed regions are removed more rapidly in the developer than the exposed regions. Development is carried for a long enough time to remove the unexposed regions in the developer, but not long enough to remove the exposed regions. The preferred time in the developer is from about 10 to 120 seconds. Hence the unexposed regions are described as being "soluble" or "removable" in the developer because they are removed, and dissolved and/or dispersed, more rapidly in the developer than the exposed regions.

A conventionally known aqueous alkaline solution can be used as a developer or a replenisher for an image recording material of the present invention. Examples include inorganic alkaline salts such as sodium silicate, potassium silicate, sodium tertiary phosphate, potassium tertiary phosphate, ammonium tertiary phosphate, sodium secondary phosphate, potassium secondary phosphate, ammonium secondary phosphate, sodium carbonate, potassium carbonate, ammonium carbonate, sodium hydrogencarbonate, potassium hydrogencarbonate, ammonium hydrogencarbonate, sodium borate, potassium borate, ammonium borate, sodium hydroxide, ammonium hydroxide, potassium hydroxide, and lithium hydroxide. Furthermore, also used are organic alkaline agents such as monomethyl amine, dimethyl amine, trimethyl amine, monoethyl amine, diethyl amine, triethyl amine, monoisopropyl amine, diisopropyl amine, triisopropyl amine, n-butyl amine, monoethanol amine, diethanol amine, triethanol amine, monoisopropanol amine, diisopropanol amine, ethylene imine, ethylene diamine, and pyridine.

These alkaline agents can be used alone or in a combination of two or more.

Furthermore, it is known that, in a case in which an automatic developing machine is used for developing, by adding to the developer an aqueous solution (replenisher) whose alkaline is stronger than that of the developer, a large amount of planographic printing plates can be developed without changing the developer in the developing tank for a long time. The replenishing method is also preferably applied in the present invention.

Various types of surfactants and organic solvents can be added to a developer or a replenisher for promoting or curbing the developing property, improving the dispersion of developing scum or conformity of the printing plate image portion to ink as needed. Examples of preferable surfactants include anionic surfactants, cationic surfactants, nonionic surfactants, and ampholytic surfactants.

Furthermore, reducing agents such as a sodium salt or a potassium salt of an inorganic acid including hydroquinone, resorcin, sulfurous acid, and hydrogen sulfurous acid, organic carboxylic acid, antifoaming agents, and water softeners can be added to a developer or a replenisher as needed.

Useful developers are aqueous solutions having a pH of about 7 or above. Preferred aqueous alkaline developers are those that have a pH between 8 and about 13.5, typically at least about 11, preferably at least about 12. Useful developers include commercially available developers such as PC9000, PC3000, PC955, PC592, Goldstar, Greenstar, ThermalPro, Protherm, MX1710, and 956 aqueous alkaline developers each available from Kodak Polychrome Graphics LLC. Developers are described for example in Yamasue, US 4259434, Seino US4452880, Miller US 5851735, Eckler US5998102, Miro US EP-A-0732628, Toyama, GB-A-2276729 and Fiebag US6143479.

Development is typically carried out in a processor equipped with an immersion type developing bath, a section for rinsing with water, a gumming section, a drying section and a conductivity measuring unit. Typically the developer is applied to the imaged precursor by rubbing or wiping the element with an applicator containing the developer. Alternatively, the imaged precursor may be brushed with the developer or the developer may be applied to the precursor by spraying the element with sufficient force to remove the unexposed regions. In either instance, a printing plate is produced. Development may be carried out in a commercially available processor, such as a Mercury V Processor and (available from Kodak Polychrome Graphics) and a Quartz K85 Processor (available from Glunz and Jensen of Norfolk, UK). Preferably, the developer temperature is from about 10° C. to about 50° C., more preferably about 15° C. to about 35° C. Following development, the printing plate is rinsed with water and dried. Drying may be conveniently carried out by IR heaters or with hot air. After drying, the printing plate may be treated with a gumming solution. A gumming solution comprises one or more water soluble polymers, for example polyvinylalcohol, polymethacrylic acid, polymethacrylamide, polyhydroxyethylmethacrylate, polyvinylmethacrylate, gelatin and polysaccharide such as dextrin, pullulan, cellulose, gum arabic and alginic acid. A preferred material is gum arabic.

While post-development heating or other operation is normally not necessary for this invention, such operations may be preferred for some applications.

The images obtained by the above described processing are suitable for many uses. For example, in the case of using a simple aluminum plate as the base, good prints are obtained by applying it to a printing machine after carrying out development. Further, a material prepared by providing a sensitive layer containing dyes on a transparent plastic film such as a polyester film can be used for correction of prints. In addition, it is possible to use photomasks, laser recording of output signals of computers and facsimile recording materials.

Moreover, the base of the developed sensitive material may be subjected to various processings according to the purpose. For example, in case of using a glass plate having a chromium vacuum deposition layer as the base, the chromium deposition layer is etched with a known etching solution containing ceric ion after the sensitive layer is developed to form a etching resist, and the resist layer is then removed, by which the base can be used as a hard mask. In case of using a silicon plate as the base, it is possible to make an etching resist of the silicon oxide layer or to use for a lift-off step. In case of using a copper foil plate for making a print circuit plate, it is possible to use as an etching resist or a plating resist after development.

The present invention is further described in detail by means of the following Examples and Comparisons. All parts and percentages are by weight and all temperatures are degrees Celsius unless explicitly stated otherwise.

EXAMPLES

Synthesis Example 1

Synthesis of 2-methoxy-4-(phenylamino)-benzenediazonium dodecyl sulfate (MSDS) acid generator. 16.0 g of sodium dodecyl sulfate (Aldrich, Milwaukee, Mich.) in 300 ml of water was slowly added into 18.0 g of 2-methoxy-4-phenylamino)-benzenediazonium bisulfate (Diverstec, Fort Collins, Colo.) in 300 ml of water while stirring. The mixture was stored in dark at 0–5° C. for 5 hours. After decanting water, the resulting oil material was dissolved in 100 ml ethyl acetate. The solution was washed with 50 ml of 5% NaHCO$_3$ and then with 50 ml of water. The organic layer was dried over anhydrous MgSO$_4$ for 6 hours, and the solvent was removed by vacuum. 12.8 g of oil material was obtained.

Proton NMR (in acetone-d$_6$): δ 0.88 (3H,t), 1.32 (18H, m), 1.58 (2H, m), 3.91 (2H, t), 4.15 (3H,s), 6.90–7.55 (7H, m), 8.18 (1H, d), and 11.12 (1H,s).

Synthesis Example 2

Synthesis of 2-methoxy-4-(phenylamino)-benzenediazonium hexadecyl sulfate (MSHDS) acid generator. 3.25 g of 2-methoxy-4-(phenylamino)-benzenediazonium bisulfate (Diverstec, Fort Collins, Colo.) in 50 ml of water was neutralized with 0.8 g of NaHCO$_3$ in 25 ml water, and marked the container with A. 3.45 g of sodium hexadecyl sulfate (TCI America, Portland, Oreg.) was dissolved in 150 ml of water AT 50° C., and marked the container with B. While stirring, solution A was slowly added into solution B and the precipitate was formed after mixing was completed. The reaction mixture was stored in dark at 0–5° C. for 12 hours. The solid was collected by filtration and then dried by vacuum. The yield was 5.4 g.

Proton NMR (in acetone-d$_6$): δ 0.87(3H,t), 1.31 (26H, m), 1.58 (2H, m), 3.90 (2H, t), 4.15 (3H,s), 6.90–7.60 (7H, m), 8.19 (1H, d), and 11.10 (1H,s).

Synthesis Example 3

Synthesis of 2-methoxy-4-(phenylamino)-benzenediazonium vinyl benzyl thiosulfate (MSVBTS) acid generator. 0.50 g of sodium vinyl benzyl thiosulfate (Eastman Kodak Company, Rochester, N.Y., U.S. Pat. No. 5,985,514) in 100 ml of water was slowly added into 25 ml of 5% 2-methoxy-4-(phenylamino)-benzenediazonium bisulfate (Diverstec, Fort Collins, Colo.) while stirring. The mixture was stored in dark at 0–5° C. for 24 hours. After decanting water, the resulting oil material was washed with 10 ml water three times. 1.13 g of oil material was obtained and was then dissolved in 99 g of 1-methoxy-2-propanol for further use.

Example 4

Synthesis of 2-methoxy-4-(phenylamino)-benzenediazonium octyl sulfate (MSOS) acid generator. 64.0 g of 35% sodium octyl sulfate (Aldrich, Milwaukee, Mich.) in water was slowly added in 31.0 g of 2-methoxy-4-(phenylamino)-benzenediazonium bisulfate (Diverstec, Fort Collins, Colo.) in 500 ml of water while stirring. The mixture was stored in dark at 0–5° C. for 5 hours. After decanting water, the resulting oil material was dissolved in 200 ml ethyl acetate. The solution was washed with 50 ml of 5% NaHCO$_3$ and then with 50 ml of water. The organic layer was dried over anhydrous MgSO$_4$ for 6 hours, and the solvent was removed by vacuum. 35.1 g of oil material was obtained.

Proton NMR (in acetone-d$_6$): δ 0.84 (3H,t), 1.22 (10H, m), 1.53 (2H, p), 3.88 (2H,t), 4.10 (3H,s), 6.50–7.60 (7H, m), 8.17 (1H, d), and 10.9 (1H,s).

Example 5

Preparation of the Lithographic Plates

A coating solution was prepared by dissolving 6.8 g of 25% resole (GP649D99 resole resin from Georgia-Pacific, Atlanta, Ga.), 8.4 g of 34% N-13 novolak (Eastman Kodak Company, Rochester, N.Y.), 0.75 g of MSHDS prepared above, 0.47 g of Trump IR dye[1] (Eastman Kodak Company, Rochester, N.Y.), 0.39 g of terephthaldicarboxaldehyde (Aldrich, Milwaukee, Wis.), 0.02 g of D11 colorant dye (PCAS, Longjumeau, France), and 0.2 g of 10% Byk-307 (Byk-Chemie, Wallingford, Conn.) in 80 g of 1-methoxy-2-propanol and 3 g of acetone. An electrochemically grained and anodized aluminum substrate, post-treated with polyvinylphosphoric acid (PVPA), was coated with above solution with a dry coating weight of about 130 mg/ft². When properly dried at 190° F. for about 2 minutes on a rotating drum, the resulting plate was placed on a CREO Trendsetter 3244x image setter (CreoScitex, Burnaby, British Columbia, Canada) and exposed to 830 nm IR laser at a drum speed of 165 rpm and a series of laser power from 3 to 14 W (ranged from 40 to 180 mJ/cm²). The minimum exposure energy to achieve maximum processed density was about 65 mJ/cm². The plate was preheated in a SPC Mini-HD Oven (Wisconsin Oven Corp., East Troy, Wis.) at 260° F. for about 2 minutes and was subsequently developed through a Unigraph Quartz K85 processor (Glunz & Jensen, Norfolk, England) charged with ThermalPro developer (manufactured by Kodak Polychrome Graphics, Norwalk, Conn.) at 25° C. The developed plate was mounted on a Miehle sheet-fed press to produce about 20,000 good impressions using a black ink containing 1.5% of calcium carbonate.

[1]"2-[2-[2-chloro-3-[2-(1,3-dihydro-1,3,3-trimethyl-2H-benzeindol-2-ylidene)ethylidene]-1-cyclohexen-1-yl]ethenyl]-1,3,3-trimethyl-1H-benzeindolium 4-methylbenzenesulfonate"

The plate can alternatively be imaged by UV radiation. An UV exposure was accomplished by exposing the plate prepared above on an Olec Light Integrator (OLEC Corporation, Irvine, Calif.) with 25 units, and an eight to twelve sensitivity was achieved based on a T-14 grayscale.

Example 6

A coating solution was prepared by dissolving 13.7 g of 25% resole (GP649D99 resole resin from Georgia-Pacific), 16.8 g of 34% N-13 novolak (Eastman Kodak Company), 76.7 g of 1.1% MSVBTS prepared above, 0.94 g of Trump IR dye[2] (Eastman Kodak Company), 0.78 g of terephthaldicarboxaldehyde (Aldrich), 0.08 g of D11 colorant dye (PCAS), and 0.4 g of 10% Byk-307 (Byk Chemie) in 60 g of 1-methoxy-2-propanol and 6 g of acetone. An electrochemically grained and anodized aluminum substrate was coated with above solution with a dry coating weight of about 130 mg/ft². The plates were imaged digitally as described in Example 5. The minimum exposure energy to achieve maximum image density was about 65 mJ/cm². The plate can alternatively be imaged by UV radiation. An UV exposure was accomplished by exposing the plate prepared above on an Olec Light Integrator (OLEC Corporation, Irvine, Calif.) with 25 units, and an eight to twelve sensitivity was achieved based on a T-14 grayscale.

[2] "2-[2-[2-chloro-3-[2-(1,3-dihydro-1,3,3-trimethyl-2H-benzeindol-2-ylidene)ethylidene]-1-cyclohexen-1-yl]ethenyl]-1,3,3-trimethyl-1H-benzeindolium 4-methylbenzenesulfonate"

Example 7

A coating solution was prepared by dissolving 6.8 g of 25% resole (GP649D99 resole resin from Georgia-Pacific, Atlanta, Ga.), 8.4 g of 34% N-13 novolak (Eastman Kodak Company, Rochester, N.Y.), 0.65 g of MSDS prepared in Synthesis Example 1, 0.47 g of TRUMP IR Dye[3] (Eastman Kodak Company, Rochester, N.Y.), 0.39 g of terephthaldicarboxaldehyde (Aldrich, Milwaukee, Wis.), 0.02 g of D11 colorant dye (PCAS, Longjumeau, France), and 0.2 g of 10% Byk-307 (Byk-Chemie, Wallingford, Conn.) in 80 g of 1-methoxy-2-propanol and 3 g of acetone. An electrochemically grained and anodized aluminum substrate, post-treated with polyvinylphosphoric acid (PVPA), was coated with above solution with a dry coating weight of about 130 mg/ft². The plates were imaged digitally as described in Example 5. The minimum exposure energy to achieve maximum image density was about 65 mJ/cm². The plate can alternatively be imaged by UV radiation. An UV exposure was accomplished by exposing the plate prepared above on an Olec Light Integrator (OLEC Corporation, Irvine, Calif.) with 25 units, and an eight to twelve sensitivity was achieved based on a T-14 grayscale.

[3] "2-[2-[2-chloro-3-[2-(1,3-dihydro-1,3,3-trimethyl-2H-benzeindol-2-ylidene)ethylidene]-1-cyclohexen-1-yl]ethenyl]-1,3,3-trimethyl-1H-benzeindolium 4-methylbenzenesulfonate"

Example 8

A coating solution was prepared by dissolving 6.8 g of 25% resole (GP649D99 resole resin from Georgia-Pacific, Atlanta, Ga.), 8.4 g of 34% N-13 novolak (Eastman Kodak Company, Rochester, N.Y.), 0.52 g of MSOS prepared in Synthesis Example 4, 0.47 g of Trump IR Dye[4] (Eastman Kodak Company, Rochester, N.Y.), 0.39 g of terephthaldicarboxaldehyde (Aldrich, Milwaukee, Wis.), 0.02 g of D11 colorant dye (PCAS, Longjumeau, France), and 0.2 g of 10% Byk-307 (Byk-Chemie, Wallingford, Conn.) in 80 g of 1-methoxy-2-propanol and 3 g of acetone. An electrochemically grained and anodized aluminum substrate, post-treated with polyvinylphosphoric acid (PVPA), was coated with above solution with a dry coating weight of about 130 mg/ft². The plates were imaged digitally as described in Example 5. The minimum exposure energy to achieve maximum image density was about 65 mJ/cm². The plate can alternatively be imaged by UV radiation. An UV exposure was accomplished by exposing the plate prepared above on an Olec Light Integrator (OLEC Corporation, Irvine, Calif.) with 25 units, and an eight to twelve sensitivity was achieved based on a T-14 grayscale.

[4] "2-[2-[2-chloro-3-[2-(1,3-dihydro-1,3,3-trimethyl-2H-benzeindol-2-ylidene)ethylidene]-1-cyclohexen-1-yl]ethenyl]-1,3,3-trimethyl-1H-benzeindolium 4-methylbenzenesulfonate"

When Examples 5 to 8 are conducted with UV imaging, the IR dye employed therein is non-critical.

Example 9

A coating solution was prepared by dissolving 6.8 g of 25% resole (GP649D99 resole resin from Georgia-Pacific, Atlanta, Ga.), 8.4 g of 34% N-13 novolak (Eastman Kodak Company, Rochester, N.Y.), 0.52 g of MSHDS prepared above, 0.39 g of terephthaldicarboxaldehyde (Aldrich, Milwaukee, Wis.), 0.02 g of D11 colorant dye (PCAS, Longjumeau, France), and 0.2 g of 10% Byk-307 (Byk-Chemie, Wallingford, Conn.) in 80 g of 1-methoxy-2-propanol and 3 g of acetone. An electrochemically grained and anodized aluminum substrate, post-treated with polyvinylphosphoric acid (PVPA) was coated with above solution with a dry coating weight of about 130 mg/ft2. An UV exposure was accomplished by exposing the plate prepared above on an Olec Light Integrator (OLEC Corporation, Irvine, Calif.) with 25 units, and an eight to thirteen sensitivity was achieved based on a T-14 grayscale.

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. An acid generating agent useful for imaging photosensitive elements selected from compounds of the formula;

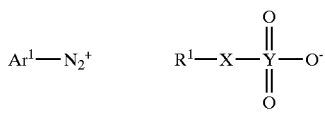

wherein:
R$^1$ is an unsubstituted or substituted alkyl group or an unsubstituted or substituted aryl group;
X is selected from the group consisting of oxygen and sulfur;
Y is sulfur; and
Ar$^1$ an unsubstituted or substituted aryl group.

2. The acid generating agent of claim 1 wherein X is oxygen.

3. The acid generating agent of claim 2 wherein R$^1$ is octyl.

4. The radiation-sensitive patterning composition of claim 3 wherein Ar$^1$—N$_2^+$ is 2-methoxy-4-(phenylamino)-benzenediazonium.

5. The acid generating agent of claim 1 wherein X is sulfur.

6. The acid generating agent of claim 1 wherein R$^1$ is an alkyl group or aryl group having 1 to 50 carbon atoms.

7. The acid generating agent of claim 1 wherein R$^1$ is selected from the group consisting of methyl, ethyl, n-propyl, isopropyl, allyl, n-butyl, sec-butyl, t-butyl, hexyl, cyclohexyl, heptyl, octyl, 2-ethylhexyl, nonyl, decyl, dodecyl, hexadecyl, octadecyl, vinyl, 1-methylvinyl, 2-phenylvinyl, benzyl, vinyl benzyl, phenethyl, phenyl, tolyl, xylyl, cumenyl, mesityl, dodecylphenyl, phenylphenyl, naphthyl, and anthracenyl.

8. The acid generating agent of claim 2 wherein R$^1$ is selected from the group consisting of hexyl, cyclohexyl, heptyl, octyl, 2-ethylhexyl, nonyl, decyl, dodecyl, hexadecyl, and octadecyl.

9. An acid generating agent selected from the group consisting of compounds of the formula:

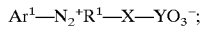

wherein: Ar$^1$—N$_2^+$ is 2-methoxy-4-(phenylamino)-benzenediazonium;
R$^1$ is an unsubstituted or substituted alkyl group or an unsubstituted or substituted aryl group;
X is selected from the group consisting of oxygen, sulfur and selenium; and
Y is selected from the group consisting of sulfur, selenium and tellurium.

10. The acid generating agent of claim 9 wherein the R$_1$ is selected from the group consisting of hexyl, cyclohexyl, heptyl, octyl, 2-ethylhexyl, nonyl, decyl, dodecyl, hexadecyl, and octadecyl.

11. The acid generating agent of claim 9 wherein the agent is selected from the group consisting of 2-methoxy-4-(phenylamino)-benzenediazonium dodecyl sulfate; 2-methoxy-4-(phenylamino)-benzenediazonium hexadecyl sulfate; and 2-methoxy-4-(phenylamino)-benzenediazonium octyl sulfate.

12. The acid generating agent of claim 9 wherein the agent is 2-methoxy-4-(phenylamino)-benzenediazonium vinyl benzyl thiosulfate.

13. A radiation-sensitive patterning composition comprising:
(1) at least one acid generating compound selected from the compounds of formulae (I), (II), and (III):

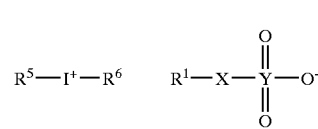

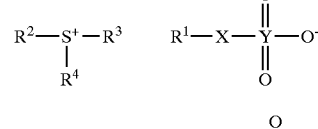

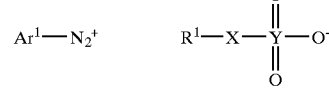

(2) at least one cross-linking agent cross-linkable by the acid;
(3) at least one polymer compound having at least one functional group capable of reading with the cross-linking agent; and
(4) at least one infrared absorbing agent;
wherein:
R$^1$ is an unsubstituted or substituted alkyl group or an unsubstituted or substituted aryl group;
X is selected from the group consisting of oxygen, sulfur and selenium;
Y is selected from the group consisting of sulfur, selenium and tellurium;
Ar$^1$ is an unsubstituted and substituted aryl group;
R$^2$, R$^3$ and R$^4$ are each individually an unsubstituted or substituted alkyl group or an unsubstituted or substituted aryl group or any two of them are bonded together to form a ring structure; and
R$^5$ and R$^6$ are each individually an unsubstituted or substituted alkyl group or an unsubstituted or substituted aryl group, or are bonded to each other to form a ring structure.

14. The radiation-sensitive patterning composition of claim 13 wherein X is oxygen and Y is sulfur.

15. The radiation-sensitive patterning composition of claim 13 wherein X and Y are each sulfur.

16. The radiation-sensitive patterning composition of claim 13 wherein R$^1$ is an alkyl group or aryl group having 1 to 50 carbon atoms.

17. The radiation-sensitive patterning composition of claim 13 wherein X is oxygen, Y is sulfur, and R$^1$ is an alkyl group or aryl group having 1 to 50 carbon atoms.

18. The radiation-sensitive patterning composition of claim 13 wherein X and Y are each sulfur, and R$^1$ is an alkyl group or aryl group having 1 to 50 carbon atoms.

19. The radiation-sensitive patterning composition of claim 13 wherein the acid generating compound has the formula (III) and Ar$^1$—N$_2^+$ is 2-methoxy-4-(phenylamino)-benzenediazonium.

20. The radiation-sensitive patterning composition of claim 13 wherein X is oxygen, Y is sulfur, and R$^1$ is octyl, dodecyl, or hexadecyl.

21. The radiation-sensitive patterning composition of claim 13 wherein the acid generating compound is selected from the group consisting of 2-methoxy-4-(phenylamino)-benzenediazonium dodecyl sulfate; 2-methoxy-4-(phenylamino)-benzenediazonium hexadecyl sulfate; and 2-methoxy-4-(phenylamino)-benzenediazonium octyl sulfate.

22. The radiation-sensitive patterning composition of claim 13 wherein the acid generating compound is 2-methoxy-4-(phenylamino)-benzenediazonium vinyl benzyl thiosulfate.

23. The radiation-sensitive patterning composition of claim 13 wherein the acid generating compound comprises about 0.01% to about 50% by weight of the solid components of the radiation-sensitive composition; the cross-linking agent comprises about 5% to 70% by weight of the solid components of the radiation-sensitive composition; the polymer compound comprises about 10% to about 90% by weight of the solid components of the radiation-sensitive composition; and the infrared absorbing agent comprises about 0.01% to about 50% by weight of the solid components of the radiation-sensitive composition.

24. The radiation-sensitive patterning composition of claim 13 wherein the cross-linking agent is a resole resin and the polymer compound having at least one functional group capable of reacting with the cross-linking agent is a novolak resin.

25. The radiation-sensitive patterning composition of claim 13 wherein the polymer compound is a polymer compound having an alkaline-soluble group.

26. A radiation-sensitive patterning composition comprising:
(1) at least one acid generating compound selected from the compounds of formulae (I), (II), and (III):

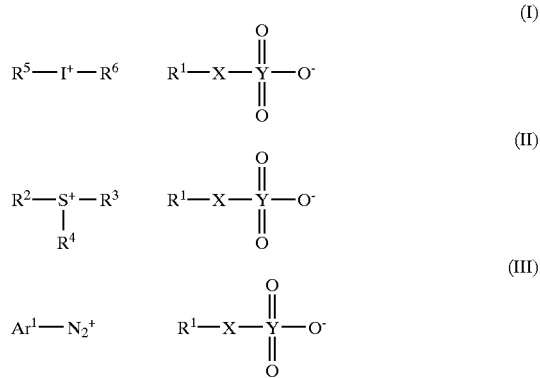

(2) at least one cross-linking agent cross-linkable by the acid; and
(3) at least one polymer compound having at least one functional group capable of reacting with the cross-linking agent;
wherein:
$R^1$ is an unsubstituted or substituted alkyl group or an unsubstituted or substituted aryl group;
X is selected from the group consisting of oxygen, sulfur and selenium;
Y is selected from the group consisting of sulfur, selenium and tellurium;
$Ar^1$ is an unsubstituted and substituted aryl group;
$R^2$, $R^3$ and $R^4$ are each individually an unsubstituted or substituted alkyl group or an unsubstituted or substituted aryl group or any two of them are bonded together to form a ring structure; and
$R^5$ and $R^6$ are each individually an unsubstituted or substituted alkyl group or an unsubstituted or substituted aryl group, or are bonded to each other to form a ring structure.

27. The radiation-sensitive patterning composition of claim 26 wherein X is oxygen and Y is sulfur.

28. The radiation-sensitive patterning composition of claim 26 wherein X and Y are each sulfur.

29. The radiation-sensitive patterning composition of claim 26 wherein $R^1$ is an alkyl group or aryl group having 1 to 50 carbon atoms.

30. The radiation-sensitive patterning composition of claim 26 wherein X is oxygen, Y is sulfur, and $R^1$ is an alkyl group or aryl group having 1 to 50 carbon atoms.

31. The radiation-sensitive patterning composition of claim 26 wherein X and Y are each sulfur, and $R^1$ is an alkyl group or aryl group having 1 to 50 carbon atoms.

32. The radiation-sensitive patterning composition of claim 26 wherein the acid generating compound has the formula (III) and $Ar^1$—$N_2^+$ is 2-methoxy-4-(phenylamino)-benzenediazonium.

33. The radiation-sensitive patterning composition of claim 26 wherein X is oxygen, Y is sulfur, and $R^1$ is octyl, dodecyl, or hexadecyl.

34. The radiation-sensitive patterning composition of claim 26 wherein the acid generating compound is selected from the group consisting of 2-methoxy-4-(phenylamino)-benzenediazonium dodecyl sulfate; 2-methoxy-4-(phenylamino)-benzenediazonium hexadecyl sulfate; and 2-methoxy-4-(phenylamino)-benzenediazonium octyl sulfate.

35. The radiation-sensitive patterning composition of claim 26 wherein the acid generating compound is 2-methoxy-4-(phenylamino)-benzenediazonium vinyl benzyl thiosulfate.

36. The radiation-sensitive patterning composition of claim 26 wherein the acid generating compound has the formula (III), X is oxygen, Y is sulfur, and $R^1$ is an alkyl group or aryl group having 1 to 50 carbon atoms.

37. The radiation-sensitive patterning composition of claim 36 wherein $R^1$ is selected from the group consisting of methyl, ethyl, n-propyl, isopropyl, allyl, n-butyl, sec-butyl, t-butyl, hexyl, cyclohexyl, heptyl, octyl, 2-ethylhexyl, nonyl, decyl, dodecyl, hexadecyl, octadecyl, vinyl, 1-methylvinyl, 2-phenylvinyl, benzyl, vinyl benzyl, phenethyl, phenyl, tolyl, xylyl, cumenyl, mesityl, dodecylphenyl, phenylphenyl, naphthyl, and anthracenyl.

38. The radiation-sensitive patterning composition of claim 37 wherein $Ar^1$—$N_2^+$ is 2-methoxy-4-(phenylamino)-benzenediazonium.

39. The radiation-sensitive patterning composition of claim 37 wherein the polymer compound having at least one functional group capable of reading with the cross-linking agent is a novolak resin.

40. The radiation-sensitive patterning composition of claim 39 in which the cross-linking agent is a resole resin.

41. The radiation-sensitive patterning composition of claim 40 wherein $R^1$ is selected from the group consisting of hexyl, cyclohexyl, heptyl, octyl, 2-ethylhexyl, nonyl, decyl, dodecyl, hexadecyl, and octadecyl.

42. The radiation-sensitive patterning composition of claim 41 wherein $Ar^1$—$N_2^+$ is 2-methoxy-4-(phenylamino)-benzenediazonium.

43. The radiation-sensitive patterning composition of claim 42 wherein $R^1$ is selected from the group consisting of octyl, dodecyl, and hexadecyl.

44. The radiation-sensitive patterning composition of claim 43 wherein the acid generating compound comprises about 0.01% to about 50% by weight of the solid components of the radiation-sensitive composition; the cross-linking agent comprises about 5% to 70% by weight of the solid components of the radiation-sensitive composition; and the polymer compound comprises about 10% to about 90% by weight of the solid components of the radiation-sensitive composition.

45. The radiation-sensitive patterning composition of claim 44 wherein $R^1$ is octyl.

46. The radiation-sensitive patterning composition of claim 45 additionally comprising an infrared absorbing agent.

47. A radiation-sensitive imaging element comprising a lithographic substrate having a layer of the radiation-sensitive patterning composition of claim 26 coated thereon.

48. The imaging element of claim 47 wherein the lithographic substrate is an aluminum plate.

49. The imaging element of claim 48 wherein the aluminum plate is anodized before the patterning composition is coated thereon.

50. The imaging element of claim 47 wherein the acid generating compound has the formula (III), X is oxygen, Y is sulfur, and $R^1$ is an alkyl group or aryl group having 1 to 50 carbon atoms.

51. The imaging element of claim 50 wherein $R^1$ is selected from the group consisting of methyl, ethyl, n-propyl, isopropyl, alkyl, n-butyl, sec-butyl, t-butyl, hexyl, cyclohexyl, heptyl, octyl, 2-ethylhexyl, nonyl, decyl, dodecyl, hexadecyl, octadecyl, vinyl, 1-methylvinyl, 2-phenylvinyl, benzyl, vinyl benzyl, phenethyl, phenyl, tolyl, xylyl, cumenyl, mesityl, dodecylphenyl, phenylphenyl, naphthyl, and anthracenyl.

52. The imaging element of claim 51 wherein $Ar^1$—$N_2^+$ is 2-methoxy-4-(phenylamino)-benzenediazonium.

53. The imaging element of claim 50 wherein the polymer compound having at least one functional group capable of reacting with the cross-linking agent is a novolak resin and the cross-linking agent is a resole resin.

54. The imaging element of claim 53 wherein $R^1$ is selected from the group consisting of hexyl, cyclohexyl, heptyl, octyl, 2-ethylhexyl, nonyl, decyl, dodecyl, hexadecyl, and octadecyl.

55. The imaging element of claim 54 wherein the acid generating compound comprises about 0.01% to about 50% by weight of the solid components of the radiation-sensitive composition; the cross-linking agent comprises about 5% to 70% by weight of the solid components of the radiation-sensitive composition; and the polymer compound comprises about 10% to about 90% by weight of the solid components of the radiation-sensitive composition.

56. The imaging element of claim 55 wherein $R^1$ is selected from the group consisting of octyl, dodecyl, and hexadecyl.

57. The imaging element of claim 47 wherein $Ar^1$—$N_2^+$ is 2-methoxy-4-(phenylamino)-benzenediazonium.

58. The imaging element of claim 57 wherein the radiation-sensitive patterning composition additionally comprises an infrared absorbing agent.

59. The imaging element of claim 58 wherein the polymer compound having at least one functional group capable of reacting with the cross-linking agent is a novolak resin and the cross-linking agent is a resole resin.

60. The imaging element of claim 59 wherein $R^1$ is selected from the group consisting of hexyl, cyclohexyl, heptyl, octyl, 2-ethylhexyl, nonyl, decyl, dodecyl, hexadecyl, and octadecyl.

61. The imaging element of claim 60 wherein the acid generating compound comprises about 0.01% to about 50% a by weight of the solid components of the radiation-sensitive composition; the cross-linking agent comprises about 5% to 70% by weight of the solid components of the radiation-sensitive composition; the polymer compound comprises about 10% to about 90% by weight of the solid components of the radiation-sensitive composition; and the infrared absorbing agent comprises about 0.01% to about 50% by weight of the solid components of the radiation-sensitive composition.

62. The imaging element of claim 61 wherein $R^1$ is selected from the group consisting of octyl, dodecyl, and hexadecyl.

63. The imaging element of claim 62 wherein the acid generating compound comprises about 0.1% to about 25% by weight of the solid components of the radiation-sensitive composition; the cross-linking agent comprises about 10% to 65% by weight of the solid components of the radiation-sensitive composition; the polymer compound comprises about 20% to about 85% by weight of the solid components of the radiation-sensitive composition; and the infrared absorbing agent comprises about 0.5% to about 10% by weight of the solid components of the radiation-sensitive composition.

64. A process of imaging a radiation-sensitive element comprising the steps of:
(1) providing a radiation-sensitive imaging element comprising a lithographic substrate having a layer of radiation-sensitive patterning composition of claim 26 thereon;
(2) imagewise exposing the radiation-sensitive imaging element and producing exposed and unexposed regions in the layer of radiation-sensitive patterning composition; and
(3) removing the unexposed regions of the layer of radiation-sensitive patterning composition from the lithographic substrate with a developer, and leaving an image.

65. The process of claim 64 additionally comprising, after step (2) and before step (3) of baking the radiation-sensitive patterning composition.

66. The process of claim 64 which the radiation-sensitive patterning composition additionally comprises at least one infrared absorbing agent and step (2) is carried out with infrared radiation.

67. The process of claim 64 wherein the acid generating compound has the formula (III), X is oxygen and Y is sulfur, and $R^1$ is an alkyl group or aryl group having 1 to 50 carbon atoms.

68. The process of claim 67 wherein $R^1$ is selected from the group consisting of methyl, ethyl, n-propyl, isopropyl, allyl, n-butyl, sec-butyl, t-butyl, hexyl, cyclohexyl, heptyl, octyl, 2-ethylhexyl, nonyl, decyl, dodecyl, hexadecyl, octadecyl, vinyl, 1-methylvinyl, 2-phenylvinyl, benzyl, vinyl benzyl, phenethyl, phenyl, tolyl, xylyl, cumenyl, mesityl, dodecylphenyl, phenylphenyl, naphthyl, and anthracenyl.

69. The process of claim 68 wherein $Ar^1$—$N_2^+$ is 2-methoxy-4-(phenylamino)-benzenediazonium.

70. The process of claim 69 wherein the polymer compound having at least one functional group capable of reacting with the cross-linking agent is a novolak resin.

71. The process of claim 70 wherein the developer has a pH between 8 and about 13.5.

72. The process of claim 69 in which the cross-linking agent is a resole resin.

73. The process of claim 69 additionally comprising, after step (2) and before step (3), a step of baking the radiation-sensitive patterning composition.

74. The process of claim 73 wherein the polymer compound having at least one functional group capable of reacting with the cross-linking agent is a novolak resin; the cross-linking agent is a resole resin; and the developer has a pH between 8 and about 13.5.

75. The process of claim 74 wherein $R^1$ is selected from the group consisting of hexyl, cyclohexyl, heptyl, octyl, 2-ethylhexyl, nonyl, decyl, dodecyl, hexadecyl, and octadecyl.

76. The process of claim 73 in which the radiation-sensitive patterning composition additionally comprises at least one infrared absorbing agent and step (2) is carried out with infrared radiation.

77. The process of claim 76 wherein the developer has a $R^1$ of at least about 11.

78. The process of claim 77 wherein $R^1$ is selected from the group consisting of octyl, dodecyl, and hexadecyl.

79. The process of claim 78 wherein the developer has a pH of at least 12.

80. The process of claim 79 wherein the acid generating compound comprises about 0.01% to about 50% by weight of the solid components of the radiation-sensitive composition; the cross-linking agent comprises about 5% to 70% by weight of the solid components of the radiation-sensitive composition; the polymer compound comprises about 10% to about 90% by weight of the solid components of the radiation-sensitive composition; and the infrared absorbing agent comprises about 0.01% to about 50% by weight of the solid components of the radiation-sensitive composition.

81. The process of claim 67 in which step (2) is carried out with ultraviolet or visible radiation.

82. The process of claim 81 wherein $R^1$ is selected from the group consisting of methyl, ethyl, n-propyl, isopropyl, allyl, n-butyl, sec-butyl, t-butyl, hexyl, cyclohexyl, heptyl, octyl, 2-ethylhexyl, nonyl, decyl, dodecyl, hexadecyl, octadecyl, vinyl, 1-methylvinyl, 2-phenylvinyl, benzyl, vinyl benzyl, phenethyl, phenyl, tolyl, xylyl, cumenyl, mesityl, dodecylphenyl, phenylphenyl, naphthyl, and anthracenyl.

83. The process of claim 82 wherein $Ar^1-N_2^+$ is 2-methoxy-4-(phenylamino)-benzenediazonium.

84. The process of claim 83 wherein the polymer compound having at least one functional group capable of reacting with the cross-linking agent is a novolak resin and the cross-linking agent is a resole resin.

85. The process of claim 84 additionally comprising, after step (2) and before step (3), a step of baking the radiation-sensitive patterning composition.

86. The process of claim 85 wherein the developer has a pH between 8 and about 13.5.

87. The process of claim 86 wherein $R^1$ is selected from the group consisting of hexyl, cyclohexyl, heptyl, octyl, 2-ethylhexyl, nonyl, decyl, dodecyl, hexadecyl, and octadecyl.

88. The process of claim 87 wherein the acid generating compound comprises about 0.01% to about 50% by weight of the solid components of the radiation-sensitive composition; the cross-linking agent comprises about 5% to 70% by weight of the solid components of the radiation-sensitive composition; and the polymer compound comprises about 10% to about 90% by weight of the solid components of the radiation-sensitive composition.

* * * * *

UNITED STATES PATENT AND TRADEMARK OFFICE
CERTIFICATE OF CORRECTION

PATENT NO. : 6,787,281 B2
DATED : September 7, 2004
INVENTOR(S) : Ting Tao and Jianbing Huang It is certified that error appears in the above-identified patent and that said Letters Patent is hereby corrected as shown below:

Column 21,
Line 42, delete "$Ar^{1-N}{}_2{}^{+\ is}$" and insert -- $Ar^1\text{-}N_2{}^+$ is --
Line 51, delete "wherein the $R_1$ is selected" and insert -- wherein $R_1$ is selected --

Column 22,
Line 21, delete "reading" and insert -- reacting --
Line 30, delete "and substituted" and insert -- or substituted --

Column 23,
Lines 25-36, delete "formulae (I), (II), and (III):

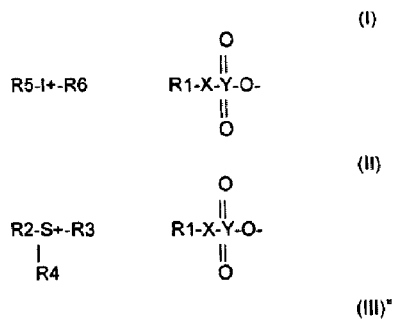

insert -- the formula --
Line 54, delete "tellurium;" and insert -- tellurirum; and --
Line 55, delete "unsubstituted and substituted" and insert -- unsubstituted or substituted. --
Line 56, delete "R2, R3 and R4 are each individually an unsubstituted or substituted alkyl group or an unsubstituted or substituted aryl group or any two of them are bonded together to form a ring structure; and R5 and R6 are each individually an unsubstituted or substituted alkyl group or an unsubstituted or substituted aryl group, or are bonded to each other to form a ring structure."

Column 24,
Line 11, delete "The acid generating compound has the formula (III) and"
Line 29, delete "the acid generating compound has the formula (III),"
Line 45, delete "reading" and insert -- reacting --

Column 25,
Line 14, delete "the acid generating compound has the formula (III),"
Line 20, delete "alkyl" and insert -- allyl --
Line 62, delete "50% a by weight" and insert -- 50% by weight --

UNITED STATES PATENT AND TRADEMARK OFFICE
CERTIFICATE OF CORRECTION

PATENT NO. : 6,787,281 B2
DATED : September 7, 2004
INVENTOR(S) : Ting Tao and Jianbing Huang It is certified that error appears in the above-identified patent and that said Letters Patent is hereby corrected as shown below:

Column 26,
Line 33, delete "step (3) of," and insert -- step (3), a step of --
Line 35, delete "64 which" and insert -- 64 in which --
Line 39, delete "the acid generating compound has the formula (III)."

Column 27,
Line 10, delete "r1" and insert -- pH --.

Signed and Sealed this

Twenty-eighth Day of June, 2005

JON W. DUDAS
*Director of the United States Patent and Trademark Office*